US00PP35142P2

(12) United States Plant Patent
Holtmaat

(10) Patent No.: US PP35,142 P2
(45) Date of Patent: Apr. 25, 2023

(54) ***HEUCHERA* PLANT NAMED 'TONCKA 380'**

(50) Latin Name: ***Heuchera* hybrid**
Varietal Denomination: Toncka 380

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 17/961,727

(22) Filed: Oct. 7, 2022

(30) Foreign Application Priority Data

Nov. 16, 2021 (QZ) ..... PBR 20212948

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — Penny J Aguirre

(57) ABSTRACT

A new cultivar of *Heuchera* plant named 'Toncka 380' that is characterized by its large leaves with a glossy surface, its leaves that are brown when young and mature to grey-green with grey-purple to black veins, its flowers that are white and red-purple in color, and its low number of inflorescences.

2 Drawing Sheets

Botanical classification: *Heuchera* hybrid.
Cultivar designation: 'Toncka 380'.

CROSS REFERENCE TO A RELATED APPLICATION

This application claims priority to European Community Plant Variety Office (CPVO) Plant Breeder's Rights Application No. No. 2021/2948, filed Nov. 16, 2021. The Applicant received the information for the Plant breeders' rights application directly from the Inventor.

BACKGROUND OF THE INVENTION

The present invention relates to a new and distinct cultivar of *Heuchera* of hybrid origin, botanically known as *Heuchera* 'Toncka 380' and is hereinafter referred to by its cultivar name 'Toncka 380'.

The new cultivar was discovered as a chance seedling in a trial field by the Inventor in Zuidwolde, The Netherlands in July of 2019. The source of the seedling was from seed collected in 2019 from open pollinated plants in a trial field that contained numerous unnamed and unpatented proprietary *Heuchera* seedlings from the Inventor's breeding program. The parentage of 'Toncka 380' is therefore unknown.

Asexual propagation of the new cultivar was first accomplished under the direction of the Inventor by tissue culture initiated from meristem tissue in February of 2020 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Toncka 380' as a new and unique cultivar of *Heuchera*.

1. 'Toncka 380' exhibits large leaves with a glossy surface.
2. 'Toncka 380' exhibits leaves that are brown when young and mature to grey-green with grey-purple to black veins.
3. 'Toncka 380' exhibits flowers that are white and red-purple in color.
4. 'Toncka 380' exhibits a low number of inflorescences.

'Toncka 380' can be most closely compared to the *Heuchera* cultivars 'Glitter' (U.S. Plant Pat. No. 25,019) and 'Silver Scrolls' (U.S. Plant Pat. No. 12,066). 'Glitter' and 'Silver Scrolls' are both similar to 'Toncka 380' in foliage coloration. 'Glitter' differs from 'Toncka 380' in having leaves that are smaller in size, shorter inflorescences, flowers that are smaller in size and pink-red in color. 'Silver Scrolls' differs from 'Toncka 380' in having leaves that are smaller in size, shorter inflorescences, and flowers that are smaller in size.

BRIEF DESCRIPTION OF THE DRAWINGS

The accompanying color photographs illustrate the overall appearance and distinct characteristics of the new *Heuchera*. The photographs were taken of a plant 18 months in age of the new cultivar as grown outdoors in a 19-cm containers in Zuidwolde, The Netherlands.

The photograph in FIG. 1 provides a side view of the plant of 'Toncka 380' in bloom.

Figure 1:
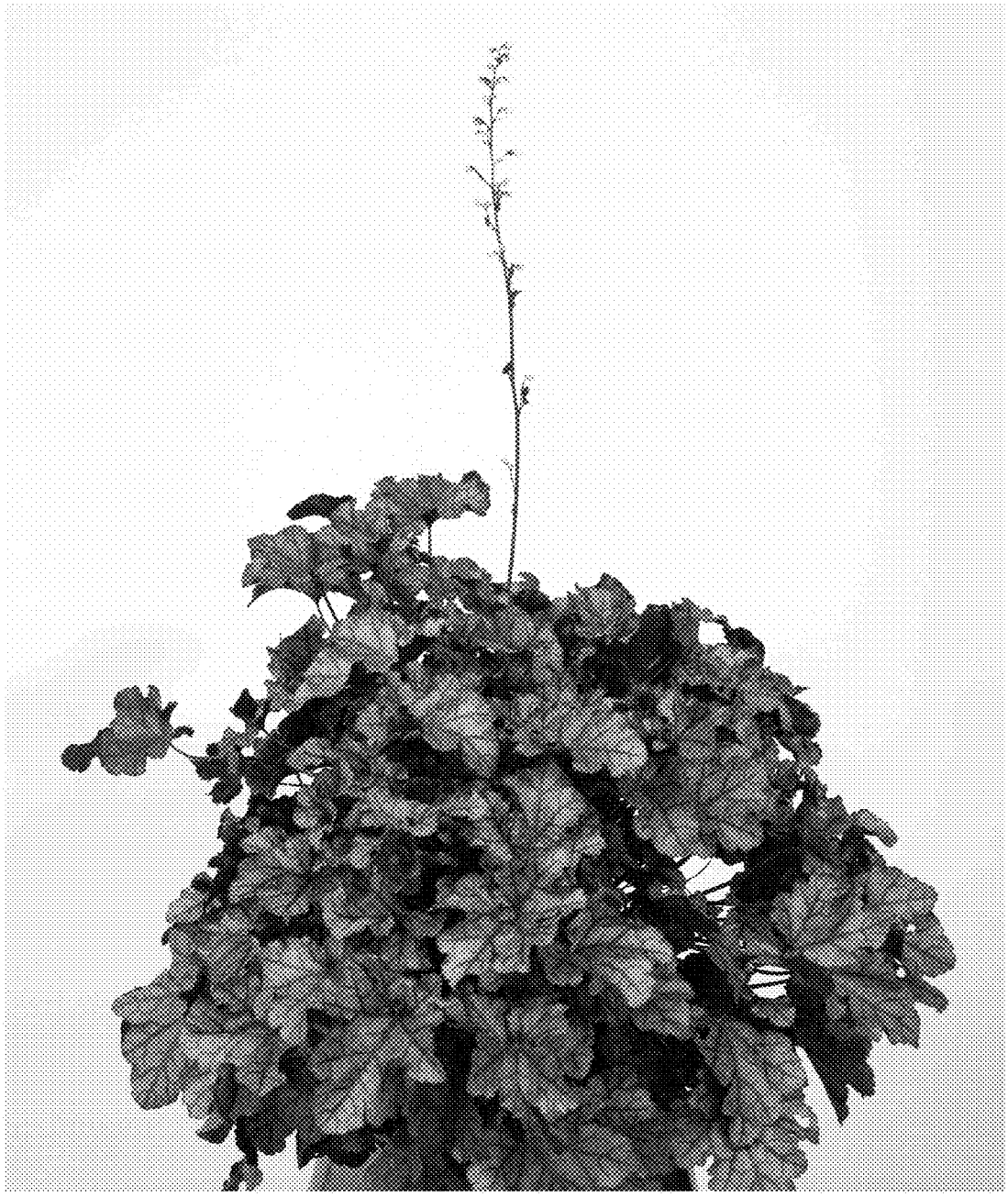
Figure 2:
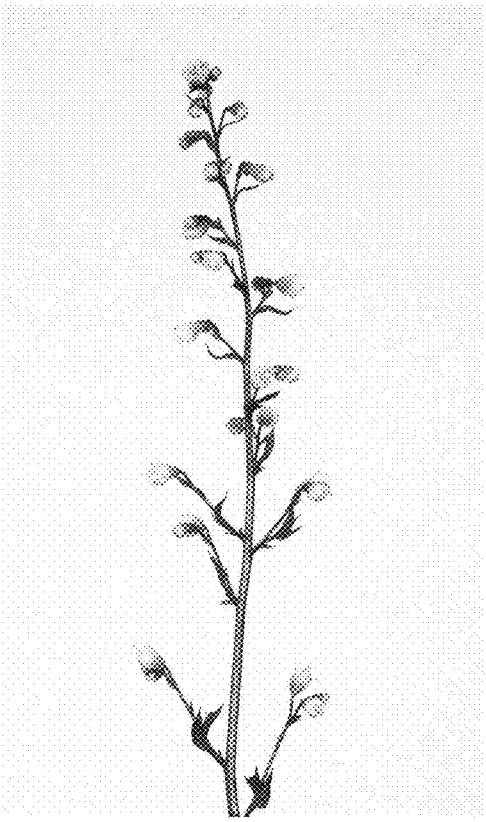

The photograph in FIG. 2 provides a close up of an inflorescence of 'Toncka 380'.

Figure 3:
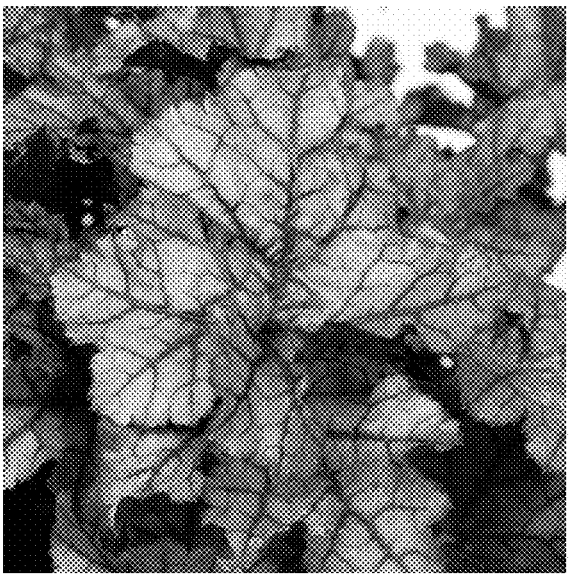

The photograph in FIG. 3 provides a close up view of the mature foliage of 'Toncka 380'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—8 weeks, midsummer in The Netherlands.

*Plant type*.—Herbaceous perennial.

*Plant habit*.—Globular with inflorescences held above the foliage.

*Height and spread*.—An average of 40 cm in height (soil level to top of foliar plane), average of 65 cm in height (soil level to top of floral plane) and 65 cm in spread as an 18 month-old plant.

*Cold hardiness*.—At least in U.S.D.A. Zone 3.

*Diseases and pests*.—No susceptibility or resistance to pests or diseases has been observed.

*Root description*.—Fibrous roots on woody rootstalks, 158D in color.

*Propagation*.—Tissue culture.

*Root development*.—An average of 3 weeks for root initiation, 6 weeks to produce a rooted cutting.

*Growth rate*.—Vigorous.

*Branching habit*.—Flowering stems emerge from basal rosette, an average of 1 rosette per plant, no lateral branches.

Foliage description:

*Leaf shape*.—Broad ovate in outline, slightly concave.

*Leaf division*.—Simple.

*Leaf base*.—Hastate, lobes touching to moderately overlapping.

*Leaf apex*.—Short and abruptly acute.

*Leaf venation*.—Laciniate, upper surface N186C, 187A, and 200A, lower surface a blend of N186A and 202A.

*Leaf margins*.—Crenate with abruptly acute tips on each tooth, strongly undulate.

*Leaf attachment*.—Petiolate.

*Leaf arrangement*.—Alternate in basal rosettes.

*Leaf lobes*.—Lobed, an average of 7 lobes, medium in depth, divergent, lobe margins free to touching.

*Leaf surface*.—Upper surface; smooth, pubescent, moderately velvety, matte, non-rugose, lower surface; smooth, pubescent, matte, non-rugose, both surfaces moderately covered with very short strigose hairs, 0.3 mm in length, closest to NN155D in color; hard to measure color based on sparseness and the small size.

*Leaf color*.—Young upper surface; N200B, young lower surface; N79B, mature upper surface; a blend of 198A and 202B, occasionally tinged N77C, mature lower surface; a blend of N186C and 187A.

*Leaf size*.—An average of 13.3 cm in length and 11.8 cm in width.

*Leaf quantity*.—An average of 8 per basal rosette.

*Petioles*.—An average of 20 cm in length and 3.5 mm in diameter, medium strength, both surfaces slightly glossy, color; upper surface 187A, lower surface 187B, tinged 177A, moderately covered with short soft hairs, average of 0.4 mm in length, hairs on both sides closest to NN155D in color; hard to measure color based on sparseness and the small size.

*Stipules*.—Leafy stipule at the base of each leaf, average 2.1 cm in length, average 5 mm in width, acute tip, 72B in color.

Flower description:

*Inflorescence type*.—Numerous small bell-shaped flowers arranged on panicles on peduncles emerging from a basal rosette.

*Inflorescence size*.—An average of 31 cm in height and 4.7 cm in diameter.

*Inflorescence number*.—An average of 1.

*Flower fragrance*.—None.

*Flower quantity*.—Average of 50 flowers per flowering stem.

*Flower Lastingness*.—Average of one week.

*Flower buds*.—Broad obovate in shape, an average of 4 mm in length and 3 mm in diameter, color; 155A, tinged at the top 58D and 150B, lower half N79C, surface is matte and densely covered with very short glandular hairs; an average of 0.2 mm in length and too small to measure color.

*Flower aspect*.—Outward to slightly nodding.

*Flower type*.—Single, campanulate.

*Flower size*.—Average of 5 mm in height and diameter.

*Petals*.—Average of 5, rotate arrangement and implanted in the hypanthium at base, oblanceolate in shape, margin is entire, apex is acute, base is long acuminate, upper and lower surface are glabrous, smooth and matte, an average of 3 mm in length and 1 mm in width, color when opening and fully open upper and lower surface; NN155D.

*Calyx*.—Campanulate, sepals fused to hypanthium, 7 mm in length, 5 mm in diameter.

*Sepals*.—An average of 5, lower 57% fused into campanulate hypanthium, short oblong in shape, an average of 7 mm in length and 2.75 mm in width, margin is entire and fused into hypanthium, apex is acute, color; when opening and fully open upper surface NN155A, slightly tinged 145C at the top, lower 57% 64C, when opening and fully open lower surface NN155B, slightly tinged 145C at the top, lower 57% 70B, both surfaces are matte and densely covered with very short glandular hairs an average of 0.2 mm in length and to small to measure color.

*Peduncle*.—An average of 62.5 cm in length and 3 mm in diameter, color; 166A, primary flower aspect 80° to horizontal, secondary peduncle aspect to main peduncle 45°, moderate in strength, surface moderately glossy and densely covered with very short soft glandular hairs; an average of 0.75 mm in length, 177C and 177D in color.

*Pedicels*.—An average of 3.5 mm in length and 0.5 mm in diameter, N186C in color, primary flower aspect straight on top of secondary pedicel, secondary and tertiary flower aspect is 25°, moderate in strength, surface matte and moderately covered with very short soft glandular hairs; average of 0.2 mm in length and too small to measure color.

Reproductive organs:

*Gynoecium*.—Pistils; 2, 4 mm in length, stigma; club-shaped, 0.2 mm in diameter, style; an average of 3.75 mm in length and NN155D in color, ovary; 72C in color.

*Androecium*.—Stamens; 5, anthers; ovate in shape, average of 0.8 mm in length, 0.4 mm in width, 199A in color, filament; 3 mm in length and NN155D in color, pollen; low in quantity, 26A in color.

*Seed/fruit*.—No fruit or seeds have been observed to date.

It is claimed:

1. A new and distinct cultivar of *Heuchera* plant named 'Toncka 380' as herein illustrated and described.

* * * * *